United States Patent [19]

Spada et al.

[11] Patent Number: 5,656,655
[45] Date of Patent: Aug. 12, 1997

[54] STYRYL-SUBSTITUTED HETEROARYL COMPOUNDS WHICH INHIBIT EGF RECEPTOR TYROSINE KINASE

[75] Inventors: Alfred P. Spada, Lansdale; Paul E. Persons, King of Prussia, both of Pa.; Alexander Levitzki, Jerusalem, Israel; Chaim Gilon, Jerusalem, Israel; Aviv Gazit, Jerusalem, Israel

[73] Assignee: Rhône-Poulenc Rorer Pharmaceuticals, Inc., Collegeville, Pa.

[21] Appl. No.: 444,696

[22] Filed: May 19, 1995

Related U.S. Application Data

[62] Division of Ser. No. 137,095, Mar. 17, 1994, Pat. No. 5,418,245.

[51] Int. Cl.$^6$ .................. C07D 209/04; A61K 31/40
[52] U.S. Cl. ......................... 514/415; 548/505
[58] Field of Search .................. 548/491, 505; 546/330; 514/357, 415

[56] References Cited

U.S. PATENT DOCUMENTS

| | | | |
|---|---|---|---|
| 3,149,148 | 9/1964 | Kladko et al. | 260/465 |
| 3,157,663 | 11/1964 | Bencze | 260/294.9 |
| 3,196,158 | 7/1965 | Bencze | 260/294.9 |
| 3,337,565 | 8/1967 | Bencze et al. | 260/294.9 |
| 3,337,568 | 8/1967 | Bencze et al. | 260/295 |
| 3,381,006 | 4/1968 | Suh | 260/240 |
| 4,600,712 | 7/1986 | Haken et al. | 514/188 |
| 4,678,793 | 7/1987 | Klaus et al. | 514/311 |
| 4,769,384 | 9/1988 | Kise et al. | 514/394 |
| 4,826,984 | 5/1989 | Berlin et al. | 546/134 |

FOREIGN PATENT DOCUMENTS

0 104 690  4/1984  European Pat. Off. .

OTHER PUBLICATIONS

Horner et al., *Liebigs Ann. Chem.* vol. 6, 1183–210 (1982).
Robinson et al., *Tetrahedron*, 45 (13), 4103–4112 (1989).
Makosza et al., *Chem. Abstracts*, 105(25) 225979N (1986).
Fuentes et al., *Chem. Abstracts*, 89(17), 146731Y (1978).
Yukhnovski et al., *Chem. Abstracts*, 77(13), 87206H (1971).
Buu–Hoi et al., *J. of the Chemical Society*, (C), 2069–70 (1969).
Fuentes et al., *Anales de Quimica*, 73, 1359–1362 (1977).
Magarian et al, *J. Pharm. Science*, vol. 58(9), pp. 1166–1167, 1969.
Birev et al., Chemical Abstract vol. 88, No. 5, Abstract 36958z, Jan. 30, 1978, p. 436.
Colau et al., Chemical Abstract, vol. 92, No. 5, Abstract 41526u, Feb. 4, 1930, p. 744.

*Primary Examiner*—Zinna Northington Davis
*Attorney, Agent, or Firm*—Synnestvedt & Lechner

[57] ABSTRACT

A method of inhibiting cell proliferation in a patient suffering from such disorder comprising the administration to the patient of a pharmaceutically effective amount of a pharmaceutical composition containing, in admixture with a pharmaceutically acceptable carrier, a compound, or a pharmaceutically acceptable salt thereof, of the formula

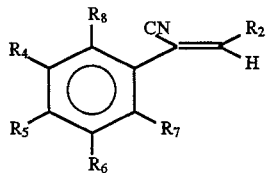

wherein the radicals are defined in the specification.

10 Claims, No Drawings

STYRYL-SUBSTITUTED HETEROARYL COMPOUNDS WHICH INHIBIT EGF RECEPTOR TYROSINE KINASE

This application is a division of Ser. No. 08/137,095 filed Mar. 17, 1994, now U.S. Pat. No. 5,418,245.

FIELD OF THE INVENTION

This invention relates to the inhibition of cell proliferation. More specifically, this invention relates to the use of styryl-substituted monocyclic and bicyclic heteroaryl compounds in inhibiting cell proliferation, including compounds which are useful protein tyrosine kinase (PTK) inhibitors.

Normal cellular reproduction is believed to be triggered by the exposure of the cellular substrate to one or more growth factors, examples of which are insulin, epidermal growth factor (EGF) and platelet-derived growth factor (PDGF). Such growth factors are typically specific for corresponding growth factor receptors which are imbedded in and which penetrate through the cellular membrane. The initiation of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylation enzymes include tyrosine kinases, which catalyze phosphorylation of tyrosine amino acid residues of substrate proteins.

Many diseased states are characterized by the uncontrolled reproduction of cells. These diseased states involve a variety of cell types and include disorders such as leukemia, cancer, psoriasis, atherosclerosis and restenosis injuries. The inhibition of tyrosine kinase is believed to have utility in the control of uncontrolled cellular reproduction, i.e., cellular proliferative disorders.

Initiation of autophosphorylation, i.e., phosphorylation of the growth factor receptor itself, and of the phosphorylation of a host of intracellular substrates are some of the biochemical events which are involved in mitogenesis and cell proliferation. Autophosphorylation of the insulin receptor and phosphorylation of substrate proteins by other receptors are the earliest identifiable biochemical hormonal responses.

Elimination of the protein tyrosine kinase (PTK) activity of the insulin receptor and of the epidermal growth factor (EGF) receptor by site-directed mutagenesis of the cellular genetic material which is responsible for generation of insulin and EGF results in the complete elimination of the receptors' biological activity. This is not particularly desirable because insulin is needed by the body to perform other biological functions which are not related to cell proliferation. Accordingly, compounds which inhibit the PTK portion of the EGF receptor at concentrations less than the concentrations needed to inhibit the PTK portion of the insulin receptor could provide valuable agents for selective treatment of cell proliferation disorders.

REPORTED DEVELOPMENTS

U.S. Pat. Nos. 4,678,793 and 4,826,984 disclose pharmaceutical compositions including styryl 4,4-dimethyl (bicyclic heteroaryl) compounds as active agents for treating cancer, psoriasis, acne, etc. U.S. Pat. No. 4,769,384 discloses pharmaceutical compositions including styryl benzimidazole compounds as active agents for treating ulcers of the stomach and duodenum.

It has been reported that the most potent inhibitors of EGF receptors inhibit EGF-induced proliferation of A431/clone 15 cells with little or no effect on the proliferation of such cells when induced by other growth factors. It has been reported also that erbstatin inhibits the autophosphorylation of the EGF receptor in membranes of A431 cells. Low concentrations of erbstatin are required to inhibit EGF receptor autophosphorylation, whereas much higher concentrations of erbstatin are required to inhibit cyclic adenosine 3',5'-monophosphate (cAMP)-dependent protein kinase.

SUMMARY OF THE INVENTION

In accordance with the present invention, there is provided a method of inhibiting cell proliferation in a patient suffering from such disorder comprising the administration to the patient of a styryl-substituted heteroaryl compound exhibiting protein tyrosine kinase inhibition activity wherein the heteroaryl group is a monocyclic ring with 1 or 2 heteroatoms, or a bicyclic ring with 1 to about 4 heteroatoms, said compound optionally substituted or polysubstituted, with the proviso that when said ring is polysubstituted, the substituents do not have a common point of attachment to said ring.

Another aspect of the present invention relates to novel compounds which are those compounds of the aforementioned type wherein no substituent on the heteroaryl group is a carboxy group or an ester group.

Still another aspect of the present invention relates to pharmaceutical compositions comprising, in admixture with a pharmaceutically acceptable carrier, a pharmaceutically-effective amount of a novel compound of the aforementioned type.

With respect to the method aspects of this invention, the compounds described by Formula I below constitute a class of the aforementioned styryl-substituted heteroaryl compounds for use in the practice of the present invention:

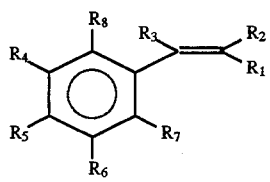

I wherein:

$R_1$ is alkyl, —H, —CN, —OH, —COOR, —CONRR or —CSNRR;

R is alkyl, —H or aralkyl;

$R_2$ is an about 5- to about 7-membered monocyclic aryl ring including 1 or 2N, O or S atoms or 1 or 2N-oxide groups, or an about 8- to about 12-membered bicyclic aryl ring including 1 to about 4N, O or S atoms or 1 to about 4N-oxide groups, said ring optionally substituted with one to about three $R_9$ groups, said $R_9$ substituents having no common points of attachment to said ring;

$R_3$ is alkyl, —H, —CN, —OH, —COOR, —CONRR, —CSNRR or —CH$_2$CN;

$R_4$, $R_5$, $R_6$, $R_7$ and $R_8$ are each independently alkyl, —H, —CN, halo, —OR, —CHO, —COOH, —NRR or an N-oxide thereof, —NO$_2$, —NHCOCH$_3$, —SR, —CF$_3$, —CH=CHCOOH, —NHCO(CH$_2$)$_2$COOH, heterocyclic or heteroaryl;

each $R_9$ is independently alkyl, —CN, halo, —OR, —CHO, —COOH, —NRR or an N-oxide thereof, —NO$_2$, —NHCOCH$_3$, —SR, —CF$_3$, —CH=CHCOOH, —NHCO(CH$_2$)$_2$COOH, heterocyclic or heteroaryl

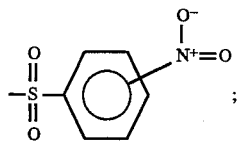

and

R$_3$ and R$_7$ together may be —CH$_2$CH$_2$—, —CH$_2$CH$_2$CH$_2$— or, starting from R$_3$, —CONH—; or a pharmaceutically acceptable salt thereof.

Also in accordance with the present invention, novel compounds within the scope of the compound and pharmaceutical composition aspects of the present invention are described by Formula I above wherein:

R$_1$ is alkyl, —CN, —COOR, —CONRR or —CSNRR;

R is alkyl, —H or aralkyl;

R$_2$ is an about 5- to about 7-membered monocyclic aryl ring including 1 or 2N, O or S atoms, or an about 8- to about 12-membered bicyclic aryl ring including 1 to about 4N, O or S atoms, said ring optionally substituted with one to about three R$_9$ groups, said R$_9$ substituents having no common points of attachment;

R$_3$ is alkyl, —H, —COOR, —CONRR, —CSNRR or —CH$_2$CN;

R$_4$ and R$_6$ are each independently alkyl, —H, —CN, halo, —OR, —CHO, —COOH, —NRR, —NO$_2$, —NHCOCH$_3$, —SR, —CF$_3$, —CH=CHCOOH, —NHCO(CH$_2$)$_2$COOH, heterocyclic or heteroaryl;

R$_5$, R$_7$ and R$_8$ are each independently alkyl, —H, —CN, —OR, —CHO, —COOH, —NHCOCH$_3$, —SR, —CF$_3$, —CH=CHCOOH, —NHCO(CH$_2$)$_2$COOH, heterocyclic or heteroaryl;

with the provisos that at least two of R$_4$, R$_5$, R$_6$, R$_7$ and R$_8$ are not —H, and R$_4$, R$_5$ or R$_6$ cannot be —OR when R$_7$ or R$_8$ is —OR; and each R$_9$ is independently alkyl, —CN, halo, —OR, —CHO, —NRR, —NO$_2$, —NHCOCH$_3$, —SR, —CF$_3$, —CH=CHCOOH, —NHCO(CH$_2$)$_2$COOH, heterocyclic heteroaryl or

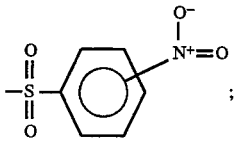

and

R$_3$ and R$_7$ together may be —CH$_2$CH$_2$—, —CH$_2$CH$_2$CH$_2$— or, starting from R$_3$, —CONH—.

In an alternate embodiment of the present invention, novel compounds within the scope of the compound and pharmaceutical composition aspects of the present invention are described by Formula II below.

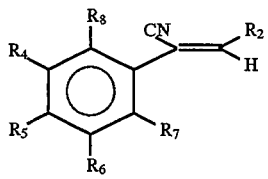

wherein:

R is alkyl, —H or aralkyl;

R$_2$ is an about 5- to about 7-membered monocyclic aryl ring including 1 or 2N, O or S atoms, or an about 8- to about 12-membered bicyclic aryl ring including 1 to about 4N, O or S atoms, said ring optionally substituted with one to about three R$_9$ groups, said R$_9$ substituents having no common points of attachment;

R$_4$ and R$_6$ are each independently branched alkyl of about 3 to about 6 carbon atoms, —CN, halo, —SR, —CF$_3$, heterocyclic, or heteroaryl;

R$_5$, R$_7$ and R$_8$ are each independently alkyl, —H, —CN, —OR, —CHO, —COOH, —NHCOCH$_3$, —SR, —CF$_3$, —CH=CHCOOH, —NHCO(CH$_2$)$_2$COOH, heterocyclic or heteroaryl;

each R$_9$ is independently alkyl, —CN, halo, —OR, —CHO, —NRR, —NO$_2$, —NHCOCH$_3$, —SR, —CF$_3$, —CH=CHCOOH, —NHCO(CH$_2$)$_2$COOH, heterocyclic, heteroaryl or

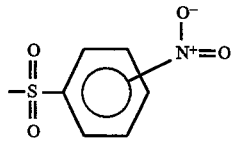

Compounds within the scope of the present invention have also a specific affinity toward the substrate site of the tyrosine kinase domain of EGF receptors, inhibit EGF receptor kinase more than they inhibit PDGF receptor kinase and also effectively inhibit EGF-dependent autophosphorylation of the receptor.

DETAILED DESCRIPTION OF THE INVENTION

As employed above and throughout the disclosure, the following terms, unless otherwise indicated, shall be understood to have the following meanings:

"Alkyl" means a saturated aliphatic hydrocarbon which may be either straight- or branch-chained containing from about 1 to about 6 carbon atoms.

"Lower alkyl" means an alkyl group as above, having 1 to about 4 carbon atoms which may be straight- or branch-chained such as methyl, ethyl, propyl, isopropyl, butyl, isobutyl, sec-butyl or tert-butyl.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Aryl" means an unsaturated or partially unsaturated ring system. Preferred aryl groups are pyridyl and indolyl.

"Heterocyclic" means an unsaturated ring system containing 1 or 2N, O or S heteroatoms. Preferred heterocyclic groups are morpholine, piperidine and piperazine.

"Acyl" means an organic radical derived from an organic acid, a carboxylic acid, by the removal of its acid hydroxyl group. Preferred acyl groups are lower alkyl carboxylic acid groups such as acetyl and propionyl. Benzoyl is also preferred.

"Halo" means a halogen. Preferred halogens include chloride, bromide and fluoride.

Preferred aralkyl groups are benzyl and phenethyl.

It is believed that therapeutically useful PTK inhibiting compounds should be competitive with the substrate of EGF receptor tyrosine kinase (EGFRK) and not with adenosine triphosphate (ATP). The PTK inhibitors quercetin and genistein, which compete with ATP, inhibit other protein kinases and as a result are highly cytotoxic. As a test of selectivity, compounds which inhibit EGFRK better than they inhibit insulin receptor kinase (IRK) and/or PDGF receptor kinase are of considerable value.

It is theorized that solubility of the compounds of the present invention both in water and in mildly hydrophobic solvents will enhance the probability that they traverse the cell membrane. Various insoluble compounds, however, have exhibited significant EGFRK inhibition in in vitro testing.

In accordance with the method aspects of the present invention, a preferred class of styryl-substituted heteroaryl compounds for use in the practice of the present invention are described by Formula II below.

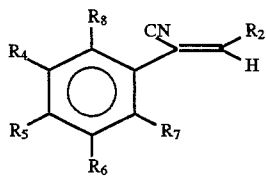

II wherein:

R is alkyl, —H or aralkyl;

$R_2$ is an about 5- to about 7-membered monocyclic aryl ring including 1 or 2N, O or S atoms or 1 or 2N-oxide groups, or an about 8- to about 12-membered bicyclic aryl ring including 1 to about 4N, O or S atoms or 1 to about 4N-oxide groups, said ring optionally substituted with one to about three $R_9$ groups, said substituents having no common points of attachment to said ring;

$R_4$, $R_5$, $R_6$, $R_7$ and $R_8$ are each independently alkyl, —H, —CN, halo, —OR, —CHO, —COOH, —NRR or an N-oxide thereof, —NO$_2$, —NHCOCH$_3$, —SR, —CF$_3$, —CH=CHCOOH, —NHCO(CH$_2$)$_2$COOH, heterocyclic, or heteroaryl;

each $R_9$ is independently alkyl, —CN, halo, —OR, —CHO, —COOH, —NRR or an N-oxide thereof, —NO$_2$, —NHCOCH$_3$, —SR, —CF$_3$, —CH=CHCOOH, —NHCO(CH$_2$)$_2$COOH, heterocyclic, heteroaryl or

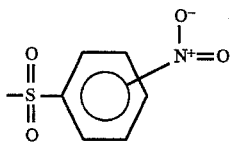

A preferred class of compounds useful in the practice of the present invention include those described by Formula I where:

$R_1$ is —CN, —COOR, —CONRR or —CSNRR;

R is lower alkyl, —H or aralkyl;

$R_2$ is a 6-membered monocyclic aryl ring including 1 or 2N, O or S atoms, or a 9- or 10-membered bicyclic aryl ring including 1–4N, O or S atoms, said ring optionally substituted with one to about three $R_9$ groups, said $R_9$ substituents having no common points of attachment to said ring;

$R_3$ is —H;

$R_4$, $R_5$, $R_6$, $R_7$ and $R_8$ are each independently lower alkyl, —H, lower alkoxy or —OH, with the provisos that at least two of $R_4$, $R_5$, $R_6$, $R_7$ and $R_8$ are not —H, and $R_4$, $R_5$ or $R_6$ cannot be lower alkoxy when $R_7$ or $R_8$ is lower alkoxy;

$R_4$ and $R_6$ are also each independently halo;

each $R_9$ is independently lower alkyl, halo, lower alkoxy, —OH or

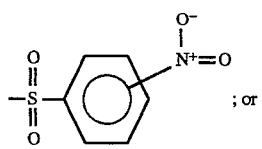

; or a pharmaceutically acceptable salt thereof.

More preferred compounds for use in the practice of this invention include those of Formulae III and IV below:

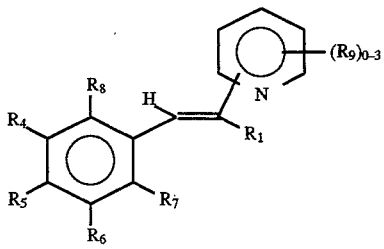

III

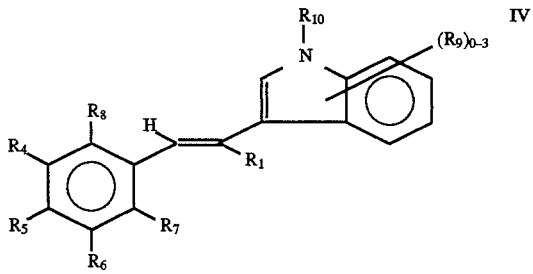

IV where $R_1$ is —CN, —COOR, —CONRR or —CSNRR;

R is lower alkyl, —H or aralkyl;

$R_2$ is a 6-membered monocyclic aryl ring including 1 or 2N, O or S atoms, or a 9- or 10-membered bicyclic aryl ring including 1–4N, O or S atoms, said ring optionally substituted with one to about three $R_9$ groups, said $R_9$ substituents having no common points of attachment to said ring;

$R_3$ is —H;

$R_4$, $R_5$, $R_6$, $R_7$ and $R_8$ are each independently lower alkyl, —H, lower alkoxy or —OH, with the provisos that at least two of $R_4$, $R_5$, $R_6$, $R_7$ and $R_8$ are not —H, and $R_4$, $R_5$ or $R_6$ cannot be lower alkoxy when $R_7$ or $R_8$ is lower alkoxy;

$R_4$ and $R_6$ are also each independently halo;

each $R_9$ is independently lower alkyl, halo, lower alkoxy, —OH or

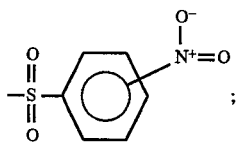

and

R$_{10}$ is —H, alkyl, aralkyl or

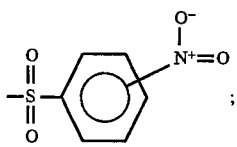

or a pharmaceutically acceptable salt thereof.

Even more preferred compounds are described by Formulae III and IV where:

R$_1$ is —CN, —COOR or —CONRR;

R$_4$, R$_5$, R$_6$, R$_7$ and R$_8$ are independently lower alkyl, —H, lower alkoxy or —OH, with the provisos that at least two of R$_4$, R$_5$, R$_6$, R$_7$ and R$_8$ are not —H, and R$_4$, R$_5$ or R$_6$ cannot be lower alkoxy when R$_7$ or R$_8$ is lower alkoxy;

R$_4$ and R$_6$ are also each independently halo;

R is lower alkyl or —H; and there are no R$_9$ substituents.

The most preferred compounds are described by Formula II where R$_1$ is —CN, R$_5$, R$_7$ and R$_8$ are each independently —H, and R$_4$ and R$_6$ are each independently alkyl, halo, —OR or —CF$_3$.

In an alternate embodiment of the present invention, a preferred class of compounds are described by Formula II above wherein R$_2$ is a 6-membered monocyclic aryl ring including 1 or 2N, O or S atoms, or a 9- or 10-membered bicyclic aryl ring including 1–4N, O or S atoms, said ring optionally substituted with one to about three R$_9$ groups, said R$_9$ substituents having no common points of attachment to said ring;

R$_4$ and R$_6$ are each independently branched lower alkyl of about 3 to about 4 carbon atoms or halo;

R$_5$, R$_7$ and R$_8$ are each independently —H lower alkyl of about 2 to about 4 carbon atoms or halo; and each R$_9$ is independently lower alkyl, halo, lower alkoxy, —OH or

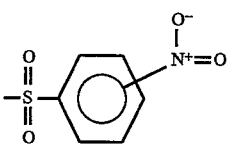

In an alternate embodiment of the present invention, more preferred compounds for use in the practice of the present invention are described by Formula V below.

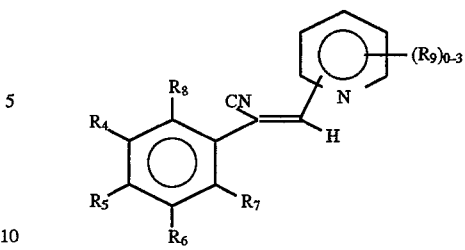

where R$_4$, R$_5$, R$_6$, R$_7$, R$_8$ and R$_9$ are as described immediately above.

In an alternate embodiment of the present invention, even more preferred compounds are described by Formula V where R$_4$ and R$_6$ are each independently halo, isopropyl, isobutyl, sec-butyl or t-butyl; R$_5$, R$_7$ and R$_8$ are each independently —H, halo, ethyl, n-propyl, isopropyl, n-butyl, isobutyl, sec-butyl or t-butyl; and there are no R$_9$ substituents.

The most preferred compounds in an alternate embodiment of the present invention are described by Formula V where R$_4$ and R$_6$ are each independently halo, and R$_5$, R$_7$ and R$_8$ are each independently —H.

Compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, lo pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Compounds useful in the pharmaceutical composition and method aspects of this invention can be prepared by known methods, for example, Knoevenagel condensation reactions such as those disclosed in U.S. Pat. No. 3,149,148.

Compounds of this invention may be prepared by the following reaction sequence:

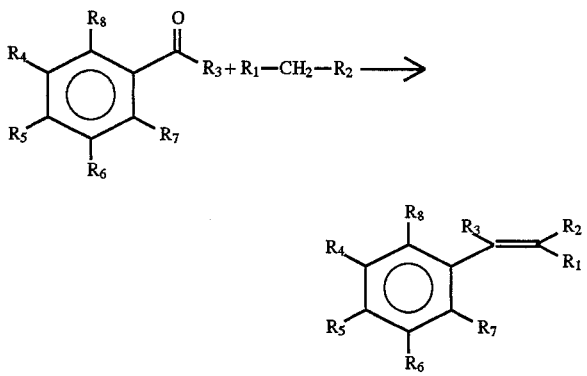

Knoevenagel condensation of a substituted benzaldehyde in a polar media with an active methylene compound of the formula $R_1CH_2R_2$ in the presence of ammonia or amines such as piperidine and raised heat results in the products of this invention. When substitution of the $R_3$ group is desired, the corresponding ketone starting material is used. Reaction temperatures in the range of 25° C. to reflux and reaction times vary depending on the materials being used in the condensation.

Compounds of this invention are either commercially available, known in the literature or can be made by known procedures. For example, U.S. Pat. No. 4,600,712 discloses fungicides of Formula I where, for example, $R_1$ is cyano, $R_2$ is pyridyl and $R_5$ and $R_7$ or $R_8$ are chloro. U.S. Pat. Nos. 3,337,565 and 3,337,568 disclose compounds which interfere with carbohydrate metabolism of Formula I where, for example, $R_2$ is cyano or hydroxy, $R_2$ is pyridyl and $R_3$ is hydroxy. U.S. Pat. No. 3,196,158 discloses adrenal cortex inhibitors of Formula I where, for example, $R_1$ is cyano, $R_2$ is pyridyl and $R_7$ or $R_8$ are halo. U.S. Pat. No. 3,157,663 discloses adrenal cortex inhibitors where, for example, $R_1$ is cyano, $R_2$ is pyridyl and $R_5$, $R_7$ or $R_8$ are amino or nitro groups. Buu-Hoi et al., *Journal of the Chemical Society* (C), pp. 2069–70 (1969) disclose the conversion of 1,2-diarylacrylonitriles to the corresponding 3-arylcoumarins, wherein the 2-aryl group bears an ortho-alkoxy-substituent. Although the foregoing publications disclose some compounds of the type that can be used in accordance with the method aspects of the present invention, they do not disclose the use of such compounds for inhibiting cell proliferation.

Various R, $R_1$, $R_3$, $R_4$, $R_5$, $R_6$, $R_7$, $R_8$ and $R_9$ substituents on the phenyl and heterocyclic ring or chain can be present in the starting compound or added after formation of the condensation product by methods known in the art for substitution or conversion on one group to another. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Tertiary amino groups can be converted to the corresponding N-oxides by oxidizing agents known in the art, for example, hydrogen peroxide and peracids. Thus, substitution or alteration reactions can be employed to provide a variety of substituents throughout the molecule of the starting material, intermediates, or the final product.

Compounds within the scope of this invention exhibit significant activity as protein tyrosine kinase inhibitors and possess therapeutic value as cellular antiproliferative agents for the treatment of certain conditions including psoriasis, atherosclerosis and restenosis injuries. It is expected that the invention will be particularly applicable to the treatment of atherosclerosis. With regard to the treatment of some conditions, for example, atherosclerosis, certain people may be identified as being at high risk, for example, due to genetic, environmental or historical factors. Compounds within the scope of the present invention can be used in preventing or delaying the occurrence or reoccurrence of such conditions or otherwise treating the condition.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food Of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be-coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the for must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached. The therapeutic human dosage based on physiological studies using rats, will generally be from about 0.01 mg to about 100 mg/kg of body weight per day or from about 0.4 mg to about 10 g or and higher although it may be administered in several different dosage units from once to several times a day. Oral administration requires higher dosages.

EXAMPLES

Embodiments of the present invention and comparative examples are described in the following non-limiting examples which include a description of pharmacological test procedures believed to correlate to therapeutic activity in humans and other animals. Examples 1 and 2 below are illustrative of compounds within the scope of the present invention. In examples 1A and 1B, $R_1$ is cyano, $R_2$ is pyridyl and $R_4$ and $R_6$ are chloro. In example 2, $R_2$ is pyridyl, $R_3$ is cyano and $R_4$ and $R_6$ are chloro.

Example 1A trans-2-(3-Pyridyl)-3-(3,5-dichlorophenyl)-2-propenenitrile

To a stirred solution of 400 g (2.3 mole) 3,5-dichlorobenzaldehyde in 11.4 liters absolute ethanol were added 283.5 g (2.4 mole) 3-pyridylacetonitrile and 720.9 g of $K_2CO_3$. Within 2 minutes of the $K_2CO_3$ addition, a solid precipitate formed. The reaction mixture was stirred about 2.5 hours. Water (22.9 liters) was added to the stirred reaction mixture. After stirring for 1 hour, the mixture was filtered and the filter cake was washed with water (10 liters), dried and recrystallized from isopropanol. Five hundred thirty four g (85% yield) of trans-2-(3-pyridyl)-3-(3,5-dichlorophenyl)-2-propenenitrile were obtained, m.p. 150°–151° C.

Example 1B cis-2-(3-pyridyl)-3-(3,5-dichlorophenyl)-2-propenenitrile

A stirred solution of trans-2-(3-pyridyl)-3-(3,5-dichlorophenyl)-2-propenenitrile (20 g), for example, as prepared in Example 1A, in 3 liters acetonitrile was irradiated with a sunlamp (275 W) for 24 hours. The reaction mixture was stirred an additional 24 hours and concentrated in vacuo. The resulting residue was purified by flash chromatography on silica gel, eluting sequentially with hexanes, 5% EtOAc/hexanes, 10% EtOAc/hexanes, and then 15% EtOAc/hexanes. The resulting yellow solid was recrystallized from 15% EtOAc/heptane to give 8 g (74% yield) of the title compound, m.p. 114°–117° C.

Example 2

2-(3,5-Dichlorophenyl)-3-(3-pyridyl)-2-propenenitrile

To a stirred solution of 3 g (17.1 mmole) of 3,5-dichlorobenzaldehyde in 200 ml absolute ethanol were added 1.83 ml (17.1 mmole) of 3-pyridyl-acetonitrile and 1 equivalent of $K_2CO_3$ (2.36 g). The reaction flask was equipped with a reflux condenser and the stirred reaction mixture was refluxed for 2 hours, filtered and concentrated. The resulting residue was purified by flash chromatography on silica gel, eluting with 4:1 hexane/ethyl acetate to give the title compound as a white solid, m.p. 139°–141° C. An amount of trans-2-(3-pyridyl)-3-(3,5-dichlorophenyl)-2-propenenitrile was also obtained from the reaction mixture.

Compounds of this invention are subjected to various biological tests, the results of which correlate to useful cellular antiproliferative activity. These tests are useful in determining EGF receptor kinase, PDGF receptor kinase and insulin receptor kinase inhibition activities of the compounds disclosed herein.

EGF-Receptor Purification

EGF-receptor purification is based on the procedure of Yarden and Schlessinger. A431 cells are grown in 80 cm$^2$ bottles to confluency ($2\times10^7$ cells per bottle). The cells are washed twice with PBS and harvested with PBS containing 1.0 mmol EDTA (1 hour at 37° C.), and centrifuged at 600 g for 10 minutes. The cells are solubilized in 1 ml per $2\times10^7$ cells of cold solubilization buffer 150 mmol Hepes buffer, pH 7.6, 1% Triton X-100, 150 mmol NaCl, 5 mmol EGTA, 1 mmol PMSF, 50 µg/ml aprotinin, 25 mmol benzamidine, 5 µg/ml leupeptic, and 10 µg/ml soybean trypsin inhibitor) for 20 minutes at 4° C. After centrifugation at 100000 g for 30 minutes, the supernatant is loaded onto a WGA-agarose column (100 µl of packed resin per $2\times10^7$ cells) and shaken for 2 hours at 4° C. The unabsorbed material is removed and the resin washed twice with HTN buffer (50 mmol Hepes, pH 7.6, 0.1% Triton X-100, 150 mmol NaCl), twice with HTN buffer containing 1M NaCl, and twice with HTNG buffer (50 mmol Hepes, pH 7.6, 0.1% Triton X-100, 150 mmol NaCl, and 10% glycerol). The EGF receptor is eluted batchwise with HTNG buffer containing 0.5M N-acetyl-D-glucosamine (200 µl per $2\times10^7$ cells). The eluted material is stored in aliquots at −70° C. and diluted before use with TMTNG buffer (50 mmol Tris-Mes buffer, pH 7.6, 0.1% Triton X-100, 150 mmol NaCl, 10% glycerol).

EGFR Kinase Catalyzed Phosphorylation of Poly (GAT) and Its Inhibition

WGA-purified EGFR (0.25 µg/assay) is preactivated with EGF (0.85 µM) in 50 mmol Tris-Mes buffer pH 7.6 for 20 minutes at 4° C. The assay is initiated by addition of a mixture which contains Mg(Ac)$_2$ (60 mmol), [γ-$^{32}$P]ATP (125 µM, 2–5 µCi/assay), poly(GAT) (0.0625 mg/ml, 0.125 mg/ml, 0.25 mg/ml), and six concentrations of inhibitor in duplicates. The temperature of the assay is 22° C. and the production of phosphorylated copolymer is found to be linear up to 20 minutes. The PTK inhibitors tested are solubilized in water or a mixture of ethanol and water such that the final concentration of ethanol does not exceed 4% in the assay. Up to 4% ethanol in the assay has no effect on the EGFR kinase activity. The concentration of EGF in the assay is 300 nM in a final volume of 40 µl. After 5, 10 or 20 minutes, aliquots of 25 µl are applied onto Whatman 3-mm paper cuttings, which are then soaked in cold 10% TCA containing 0.01M sodium pyrophosphate. After being washed overnight at 4° C., the paper cuttings are dried and counted, measuring $^{32}$P Cerenkov radiation. Concentration dependence on poly(GAT) was Michaelian with a K$_m$=0.076±0.007 mg/ml or 0.069±0.007 mmol if calculated per Glu$_6$Ala$_3$Tyr(GAT) unit. The EGF response for the poly(GAT) phosphorylation is graphed. The K$_m$ for ATP in the assay was found to 2.9 µM.

Time Dependence of EGF-Receptor Autophosphorylation

WGA-purified EGF receptor from A431 cells (0.5 µg/assay) is activated with EGF (800 nM) for 20 minutes at 4° C. The reaction is initiated by the addition of Mg(Ac)$_2$ (60 mmol Tris-Mes buffer, pH 7.6 (50 mmol), and [$^{32}$P]ATP (20 µM, 5 µCi/assay). The reaction is conducted at either 4° or 15° C. and terminated by addition of sodium dodecyl sulfate (SDS) sample buffer (10% glycerol, 50 mmol Tris, pH 6.8, 5% β-mercapto-ethanol, and 3% (SDS). The samples are run on a 8% SDS polyacrylamide gel (SDS-PAGE) (prepared from 30% acrylamide and 0.8% bis-(acrylamide) and contained 0.375M Tris, pH 8.8, 0.1% SDS, 0.05% TEMED, and 0.46% ammonium persulfate). The gel is dried and autoradiography performed with Agfa Curix RP2 X-ray film. The relevant radioactive bands are cut and counted in the Cerenkov mode. The fast phase of autophos-phorylation continues for another 10 minutes. The extent of phosphorylation completed in the first 10-s at 15° C. comprises ⅓ of the total autophosphorylation signal and probably reflects the phosphorylation of the first site on the receptor. The 10-s interval is therefore chosen for use in subsequent autophosphorylation experiments.

ATP and EGF Dependence of Autophosphorylation

WGA-purified EGF receptor from A431 cells (0.5 µg/assay is activated with EGF (0.85 µM) for 20 minutes at 4° C. The assay is performed at 15° C. and initiated by addition of Mg(Ac)$_2$ (60 mmol), Tris-Mes buffer, pH 7.6 (50 mmol), [$^{32}$P]ATP (carrier free, 5 µCi/assay), and increasing concentrations of nonradioactive ATP. The assay is terminated after 10-s by addition of SDS sample buffer. The samples are run on a 6% SDS polyacrylamide gel. The gel is dried and autoradiographed as described above. The relevant radioactive bands are cut and counted in the Cerenkov mode. the K$_m$ for ATP determined in this fashion is lo found to be 7.2 µM. With use of the 10-s assay protocol, the EGF concentration dependence of EGFRK autophosphorylation is determined.

Inhibition of Copoly(Glu$_4$Tyr) Phosphorylation by Insulin-Receptor Kinase (InsRK)

Rat liver membranes are prepared from the livers of 6-week-old rats as described by Cuatrecasas. WGA-purified insulin receptor is prepared according to Zick et al. WGA-purified rat liver InsRK (1.25 µg) is preincubated with or without 330 nM insulin in 50 mmol Tris-Mes buffer, pH 7.6, for 30 minutes at 22° C. The assay is performed at 22° C. and initiated by addition of a mixture which contains Mg(Ac)$_2$ (60 µmol), NaVO$_3$ (40 µM), [γ-$^{32}$P]ATP (125 µM, 3–5 µCi/assay), and poly(GT) [poly(Glu$_4$Tyr)] at three concentrations: whenever an inhibitor is tested, it is added at the proper concentration. The final concentration of insulin in the assay is 125 nM. The total volume of the assay is 40 µl. After 20 minutes, aliquots of 30 µl are applied on Whatman 3-mm paper and soaked in cold 10% TCA, containing 0.01M sodium pyrophosphate. After being washed overnight, the papers are dried and counted, measuring Cerenkov radiation. The InsRk-catalyzed phosphorylation of poly(GT) obeys Michaelis-Menten kinetics.

Inhibition of EGFR Autophosphorylation

A431 cells were grown to confluence on human fibronectin coated tissue culture dishes. After washing 2 times with ice-cold PBS, cells were lysed by the addition of 500 µl/dish of lysis buffer (50 mmol Hepes, pH 7 5, 150 mmol NaCl, 15 mmol MgCl$_2$, 1 mmol EGTA, 10% glycerol, 1% triton X-100, 1 mmol PMSF, 1 mg/ml aprotinin, 1 mg/ml leupeptin) and incubating 5 minutes at 4° C. After EGF stimulation (500 µg/ml 10 minutes at 37° C.) immunoprecipitation was performed with anti EGF-R (Ab 108) and the autophosphorylation reaction (50 µl aliquots, 3 µCi [γ-$^{32}$P]

ATP) sample was carried out in the presence of 2 or 10 μM of compound for 2 minutes at 4° C. The reaction was stopped by adding hot electrophoresis sample buffer. SDS-PAGE analysis (7.5% els) was followed by autoradiography and the reaction was quantitated by densitometry scanning of the x-ray films. In order to test the compounds for selective inhibition, the procedure is repeated using PDGF stimulation in place of EGF stimulation. "$IC_{50}$," as used below, refers to the concentration of inhibitor (μM) at which the rate of autophosphorylation is halved, compared with media containing no inhibitor. Preferably, the $IC_{50}$ values for EGF will be lower than for PDGF, indicating a high degree of EGF specificity of the inhibitory compounds The results of this test are summarized in Table I below.

TABLE I

| Example | $IC_{50}$ (μM) | |
|---|---|---|
|  | EGF | PDGF |
| 2 | 0.1 | 20 |
| 3 | 0.5 | 6 |
| 5 | 0.4 | 10 |
| 6 | 20 | >50 |
| 7 | 0.4 | 30 |

These results show that the compounds of the present invention inhibit EGF receptor kinase better than they inhibit PDGF receptor kinase.

Inhibition of Cell Proliferation as Measured by Inhibition of DNA Synthesis

Cells were seeded at $1 \times 10^5$ cells per well in 24-well Costar dishes pre-coated with human fibronectin (by incubating for 30 minutes at room temperature with 10 μg/0.5 ml/well). The cells were grown to confluence for 2 days. The medium was changed to DMEM containing 0.5 calf serum for 36–48 hours and the cells were then incubated with PDGF, EGF (Toyobo, New York, N.Y.) (20 ng/ml) or serum (10%. calf serum, FCS) and different concentrations of the inhibitory compounds. [$^3$H]thymidine, (NEN, Boston, Mass.) was added 16–24 hours later at 0.5 μCi/ml for 2 hours. TCA precipitable material was quantitated by scintillation counting (C). Results of this assay are summarized in Table II below. "$IC_{50}$," as used below, refers to the concentration of inhibitor (nM) at which [$^3$H]thymidine incorporation is halved, compared with media containing no inhibitor. As FCS contains a broad range of growth factors, the $IC_{50}$ values for PDGF should be lower than for FCS, indicating that the compounds do not act as general inhibitors.

TABLE II

| Example | $IC_{50}$ – PDGF | $IC_{50}$ – FCS |
|---|---|---|
| 2 | 30 ± 17 | 100 |
| 3 | 14 ± 10 | 27 ± 5% @ μM |
| 4 | 9 ± 2 | 500 |
| 6 | 17 | 15% @ 1 μM |

These results indicate that the compounds of the invention do not inhibit a broad range of growth factor receptors.

Cell Culture

Cells termed HER 14 and K721A (=DK) were prepared by transfecting N1H3T3 cells (clone 2.2) (From C. Fryling, NCI, NIH), which lack endogenous EGF-receptors, with cDNA constructs of wild-type EGF-receptor or mutant EGF-receptor lacking tyrosine kinase activity (in which Lys 721 at the ATP-binding site was replaced by an Ala residue, respectively). All cells were grown in DMEM with 10% calf serum (Hyclone, Logan, Utah).

The results obtained by the above experimental methods evidence the useful protein tyrosine kinase inhibition properties of the compounds within the scope of the present invention.

Comparative Examples

The following comparative examples illustrate the improved cell proliferation inhibition of compounds of the present invention in comparison to compounds of the prior art. In comparative Example C-1, the preparation of a prior art compound, where $R_1$ is cyano, $R_2$ is pyridyl and $R_5$ and $R_8$ are chloro is described. The inhibitory activities of the compounds of Examples 1A and 2 are compared to the inhibitory activity of the compound prepared in comparative Example C-1.

Example C-1

2-(3-pyridyl)-3-(2,4-dichlorophenyl)-2-propenenitrile

To a stirred solution of 2,4-dichlorobenzaldehyde (5.0 g, 29 mmole) and 3-pyridylacetonitrile (3.05 ml, 29 mmole) in 150 ml absolute ethenol were added 3.95 $K_2CO_3$. After stirring for about 15 minutes, a white solid precipitated out of the reaction mixture. The reaction mixture was stirred overnight and filtered. The filter cake was washed with absolute ethanol and dissolved in $CH_2Cl_2$. The $CH_2Cl_2$ solution was filtered and concentrated in vacuo. The resulting white solid was recrystallized from 3:2 hexane/ethyl acetate to give 6.0 g (76%) of the title compound.

The inhibition of EGFR autophosphorylation by the compounds of Examples 1A and 2 was compared to the prior art compound of Example C-1. The EGFR autophosphorylation inhibition was evaluated using the same procedure as described hereinbefore. The results are reported in Table III below.

TABLE III

| Example | $IC_{50}$ (μM) |
|---|---|
| 1A | 2 |
| 2 | 2–6 |
| C-1 | ≥50 |

These results demonstrate that the compounds of Examples 1A and 2 are more potent inhibitors of EGF receptor kinase than C-1.

We claim:

1. A method of inhibiting cell proliferation in a patient suffering from such disorder comprising the administration to the patient of a pharmaceutically effective amount of a pharmaceutical composition containing, in admixture with a pharmaceutically acceptable carrier, a compound, or a pharmaceutically acceptable salt thereof, of the formula

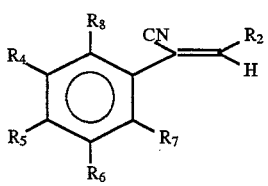

wherein:

R is alkyl, —H or aralkyl;

$R_2$ is an about 8- to about 12-membered bicyclic aryl ring including 1 to about 4N, O or S atoms or 1 to about 4N-oxide groups, said ring optionally substituted with one to about three $R_9$ groups, said $R_9$ substituents having no common points of attachment to said ring;

$R_4$, $R_5$, $R_6$, $R_7$ and $R_8$ are each independently alkyl, —H, —CN, halo, —OR, —CHO, —COOH, —NRR or an N-oxide thereof, —$NO_2$, —$NHCOCH_3$, —SR, —$CF_3$, —CH=CHCOOH, —$NHCO(CH_2)_2COOH$, heterocyclic, or heteroaryl; and each $R_9$ is independently alkyl, —CN, halo, —OR, —CHO, —COOH, —NRR or an N-oxide thereof, —$NO_2$, —$NHCOCH_3$, —SR, —$CF_3$, —CH=CHCOOH, —$NHCO(CH_2)_2COOH$, heterocyclic, heteroaryl or

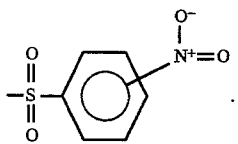

2. A compound of the formula

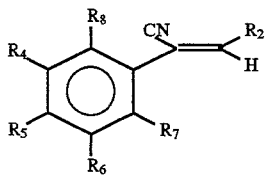

wherein:

R is alkyl, —H or aralkyl;

$R_2$ is an about 8- to about 12-membered bicyclic aryl ring including 1 to about 4N, O or S atoms, said ring optionally substituted with one to about three $R_9$ groups, said $R_9$ substituents having no common points of attachment;

$R_4$ and $R_6$ are each independently branched alkyl of about 3 to about 6 carbon atoms, —CN, halo, —SR, —$CF_3$, heterocyclic, or heteroaryl;

$R_5$, $R_7$ and $R_8$ are each independently alkyl, —H, —CN, —OR, —CHO, —COOH, —$NHCOCH_3$, —SR, —$CF_3$, —CH=CHCOOH, —$NHCO(CH_2)_2COOH$, heterocyclic or heteroaryl, provided that, when $R_2$ is quinolyl, $R_5$ is other than —OR; and each $R_9$ is independently alkyl, —CN, halo, —OR, —CHO, —NRR, —$NO_2$, —$NHCOCH_3$, —SR, —$CF_3$, —CH=CHCOOH, —$NHCO(CH_2)_2COOH$, heterocyclic, heteroaryl or

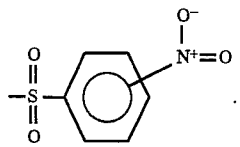

3. A pharmaceutical composition for inhibiting cell proliferation in a patient suffering from such disorder comprising, in admixture with a pharmaceutically acceptable carrier, a pharmaceutically effective amount of a compound according to claim 2.

4. A compound according to claim 2 wherein:

$R_2$ is a 9- or 10-membered bicyclic aryl ring including 1–4N, O or S atoms, said ring optionally substituted with one to about three $R_9$ groups, said $R_9$ substituents having no common points of attachment to said ring;

$R_4$ and $R_6$ are each independently branched lower alkyl of about 3 to about 4 carbon atoms or halo;

$R_5$, $R_7$ and $R_8$ are each independently —H, lower alkyl of about 2 to about 4 carbon atoms or halo; and each $R_9$ is independently lower alkyl, halo, lower alkoxy, —OH or

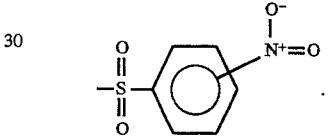

5. A method for inhibiting cell proliferation in a patient suffering from such disorder comprising administering to said patient a pharmaceutically effective amount of a compound according to claim 2.

6. A method for the treatment of psoriasis in a patient suffering from such disorder comprising administering to said patient a composition according to claim 3.

7. A method for the treatment of atherosclerosis in a patient suffering from such disorder comprising administering to said patient a composition according to claim 3.

8. A pharmaceutical composition for inhibiting in an individual a protein tyrosine kinase portion of a receptor selected from the group consisting of epidermal growth factor and platelet-derived growth factor comprising a pharmaceutically effective amount of a compound according to claim 2 and a pharmaceutically acceptable carrier.

9. A method for inhibiting, in an individual, a protein tyrosine kinase portion of a receptor selected from the group consisting of epidermal growth factor and platelet-derived growth factor comprising administering to said individual a pharmaceutically effective amount of a compound according to claim 2.

10. The method of claim 1, wherein said cell proliferation disorder is psoriasis.

* * * * *